US011998005B2

(12) United States Patent
Bevinakatti et al.

(10) Patent No.: US 11,998,005 B2
(45) Date of Patent: Jun. 4, 2024

(54) HERBICIDAL FORMULATIONS COMPRISING GLYPHOSATE AND COTE-BASED ADJUVANTS

(71) Applicant: NOURYON CHEMICALS INTERNATIONAL B.V., Arnhem (NL)

(72) Inventors: Hanamanthsa Bevinakatti, Somerset, NJ (US); Mojahedul Islam, Whitehouse Station, NJ (US)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 681 days.

(21) Appl. No.: 17/250,208

(22) PCT Filed: Jun. 13, 2019

(86) PCT No.: PCT/EP2019/065575
§ 371 (c)(1),
(2) Date: Dec. 15, 2020

(87) PCT Pub. No.: WO2019/238867
PCT Pub. Date: Dec. 19, 2019

(65) Prior Publication Data
US 2021/0186014 A1    Jun. 24, 2021

Related U.S. Application Data

(60) Provisional application No. 62/685,332, filed on Jun. 15, 2018.

(30) Foreign Application Priority Data

Aug. 10, 2018  (EP) ..................... 18188392

(51) Int. Cl.
| *A01N 25/30* | (2006.01) |
| *A01N 37/38* | (2006.01) |
| *A01N 37/40* | (2006.01) |
| *A01N 57/20* | (2006.01) |
| *C07C 217/28* | (2006.01) |
| *C07C 233/38* | (2006.01) |

(52) U.S. Cl.
CPC ............. *A01N 25/30* (2013.01); *A01N 37/38* (2013.01); *A01N 37/40* (2013.01); *A01N 57/20* (2013.01); *C07C 217/28* (2013.01); *C07C 233/38* (2013.01)

(58) Field of Classification Search
None
See application file for complete search history.

(56) References Cited

U.S. PATENT DOCUMENTS

| 3,351,574 | A | * | 11/1967 | Hicks ................. C08G 59/3218 |
| | | | | 549/555 |
| 5,296,588 | A | | 3/1994 | Au et al. |
| 9,723,841 | B2 | | 8/2017 | Zhu et al. |
| 2004/0048766 | A1 | | 3/2004 | Raths et al. |
| 2015/0164083 | A1 | | 6/2015 | Castelani et al. |
| 2015/0181865 | A1 | | 7/2015 | Schnabel et al. |

FOREIGN PATENT DOCUMENTS

| CN | 102438455 A | 5/2012 |
| CN | 102618242 A | 8/2012 |
| CN | 104084084 A | 10/2014 |
| CN | 104084085 A | 10/2014 |
| CN | 104130415 A | 11/2014 |
| CN | 106386848 A | 2/2017 |
| DE | 4238214 A1 | 5/1994 |
| JP | S63179940 | 7/1988 |
| WO | 9929171 A1 | 6/1999 |
| WO | 9955645 A1 | 11/1999 |
| WO | 200105224 A1 | 1/2001 |
| WO | 2014008562 A1 | 1/2014 |
| WO | 2016092030 A1 | 6/2016 |
| WO | 2016186529 A1 | 11/2016 |

OTHER PUBLICATIONS

EPO, European Extended Search Report issued in EP Application No. 18188392.7, dated Oct. 26, 2018.
EPO, International Search Report issued in International Application No. PCT/EP2019/065575, dated Jul. 23, 2019.
Database Registry (Online). Chemical Abstracts Service, Columbus, OH, US, Nov. 16, 1984, XP2785391, Database accession No. 67846-48-4.
Database WPI, Week 198835, Thomson Scientific, London, GB AN 1988-246770, XP2785392.
Riecers, D.E., et al. "Surfactant Effects on Glyphosate Efficacy", Weed Technology, 1995, pp. 281-285, vol. 9, No. 2.
Erisys (TM) GE-35 Castor Oil Triglycidyl Ether CAS No. 74398-71-3, Technical Bulletin, Jan. 21, 2010, pp. 1-6, XP55512849. Retrieved from the internet: URL: http://www.jiadida.com/upload/2018/0800/1355t8f2b4.pdf. Retrieved on Oct. 5, 2018.
Fairchild, J.F., et al. "Efficacy of Glyphosate and Five Surfactants for Controlling Giant Salvinia", Journal of Aquatic Plant Management, Jul. 2002, pp. 53-58, vol. 40, No. 2.
Scholnick, F., et al. "Iron Chelating Capacity of Gluconamides and Lactobionamides", Journal of Dairy Science, 1980, pp. 471-473, vol. 63., No. 3.

* cited by examiner

*Primary Examiner* — Erin E Hirt
(74) *Attorney, Agent, or Firm* — LORENZ & KOPF, LLP (57) ABSTRACT

The present disclosure generally relates to herbicidal compositions, and more particularly, herbicidal compositions comprising glyphosate or a salt thereof and a surfactant comprising at least one castor oil triglycidyl ether-based ("COTE-based") adjuvant.

19 Claims, 2 Drawing Sheets

HERBICIDAL FORMULATIONS COMPRISING GLYPHOSATE AND COTE-BASED ADJUVANTS

CROSS-REFERENCE TO RELATED APPLICATIONS

This application is a U.S. National-Stage entry under 35 U.S.C. § 371 based on International Application No. PCT/EP2019/065575, filed Jun. 13, 2019, which was published under PCT Article 21(2) and which claims priority to European Application No. 18188392.7, filed Aug. 10, 2018, and claims the benefit of U.S. Provisional Application No. 62/685,332, filed Jun. 15, 2018, which are all hereby incorporated in their entirety by reference.

TECHNICAL FIELD

The present disclosure generally relates to herbicidal compositions, and more particularly, herbicidal compositions comprising glyphosate or a salt thereof and a surfactant comprising at least one castor oil triglycidyl ether-based ("COTE-based") adjuvant.

BACKGROUND

N-phosphonomethylglycine, otherwise known as glyphosate, is well known in the art as an effective post-emergent foliar applied herbicide. Glyphosate is an organic compound with three acidic groups and in its acid form is relatively insoluble in water. Glyphosate is, therefore, normally formulated and applied as a water-soluble salt. Although monobasic, dibasic and tribasic salts of glyphosate can be made, it has generally been preferred to formulate and apply glyphosate, in the form of a monobasic salt, for example as a mono-(organic ammonium) salt such as the mono (isopropylamine) salt, often abbreviated to "IPA salt."

The present application refers to and is applicable to all glyphosate salts including, but not limited to, "ammonium", "monoammonium" and "diammonium" salts of glyphosate. For example, the glyphosate salts useful in the present context include, but are not limited to salts of isopropylamine, monoethanolamine, diethanolamine, potassium, ammonium, trimesium, or mixtures thereof. Glyphosate rates and concentrations given herein, even where the glyphosate is present as a salt or salts, are expressed as acid equivalent (a.e.) unless the context demands otherwise.

Glyphosate salts generally require the presence of a suitable surfactant to improve bioefficacy and enhance overall herbicidal performance. The surfactant may be provided in a concentrate formulation, or it may be added by the end user to a diluted spray solution. The choice of surfactant is very important since there are wide variations among surfactants in their ability to enhance the herbicidal efficacy of glyphosate, and there are a large number of surfactants that will not aid in solubilizing and improving the adjuvancy of herbicides, particularly herbicide salts.

The herbicidal efficacy of glyphosate salt solutions is highly dependent upon two factors: selecting a suitable surfactant and providing an effective (as high a concentration as possible) amount of that surfactant in the concentrate formulation. Glyphosate itself is mild to the eyes, has low aquatic toxicity and is readily biodegradable. Alkylamine based surfactants have been used and have provided excellent bioefficacy enhancing ability to glyphosate. These surfactants may under certain conditions exhibit higher eye irritation potential than various other surfactants, but are nonetheless suitable and safe for use. However, alternatives to alkylamine based surfactants having lower eye irritation properties and lower toxicity to aquatic life would be advantageous in certain circumstances.

It is known to those skilled in the art that finding a suitable surfactant with good efficacy enhancing property for glyphosate is difficult. However, finding a suitable surfactant with low eye irritation and aquatic toxicity properties in addition to good efficacy enhancing property is more difficult.

An important ingredient in many commercial glyphosate IPA formulations is tallowamine ethoxylate ("TAEO"). Such formulations show excellent bioefficacy. However, while such formulations have been approved for use by regulatory bodies around the world, concerns about their effects on humans, animals and the environment persist.

Further, although commercial glyphosate salt/TAEO formulations show excellent bioefficacy, these formulations can be limited in the amount of loading that is possible in the formulation.

Accordingly, it is desirable to develop a suitable surfactant with low eye irritation and aquatic toxicity properties in addition to good efficacy enhancing property and high loading for glyphosate. In addition, other objects, desirable features and characteristics will become apparent from the subsequent summary and detailed description, and the appended claims, taken in conjunction with the accompanying drawings and this background.

SUMMARY

This disclosure provides a surfactant compound having the Structure I:

or Structure II:

or Structure III:

Structure III wherein R¹ and R³ independently represents alkanol or ether-alkanol; and R² and R⁴ independently represents hydrogen, alkyl, alkanol or ether-alkanol.

The present disclosure generally relates in one embodiment to a surfactant compound having the Structure I:

(I)

wherein
R¹ and R³ independently represent alkanol or ether-alkanol; and
R² and R⁴ independently represent hydrogen, alkyl, alkanol or ether-alkanol.

The present disclosure relates in another embodiment to a surfactant composition comprising at least one surfactant of Structure I.

The present disclosure relates in another embodiment to a herbicidal composition comprising a herbicidally effective amount of glyphosate or a salt thereof and at least one surfactant of Structure I.

The present disclosure relates in yet another embodiment to a method of preparing a surfactant of Structure I, said method comprising (a) reacting castor oil triglycidyl ether ("COTE") with at least one primary and/or secondary amine and (b) obtaining at least one surfactant compound having the Structure I.

BRIEF DESCRIPTION OF THE DRAWING

The present disclosure will hereinafter be described in conjunction with the following drawing figures, wherein like numerals denote like elements, and.

DETAILED DESCRIPTION

The following detailed description is merely exemplary in nature and is not intended to limit the disclosure or the application and uses of the disclosure. Furthermore, there is no intention to be bound by any theory presented in the preceding background of the disclosure or the following detailed description.

The present disclosure generally relates to herbicidal formulations comprising at least one herbicidally active compound and a surfactant comprising at least one COTE-based adjuvant/surfactant.

The surfactant of Structure I is derived in the backbone from castor oil, which, in turn, is a vegetable oil obtained by pressing the seeds of the castor oil plant (*Ricinus communis*), and, thus, nontoxic and safe for both terrestrial and aquatic life. The amine termini are, in turn, derived from simple alkanol amines or sugar amines and are, thus, likewise, non-toxic and extremely safe.

Compared to TAEO, the surfactants of Structure I are less toxic and exhibit bioefficacy of the same order, but have demonstrated potential to permit stable ultrahigh glyphosate and glyphosate salt loadings of about 540 g a.e./L or higher, although lower loadings remain possible if desired.

The term "ultrahigh loading," as used herein, means a glyphosate or glyphosate salt loading of at least about 540 g a.e./L.

The term "conventional loading," as used herein, means a glyphosate or glyphosate salt loading of less than about 540 g a.e./L.

Thus, in various preferred embodiments, the herbicidally active compound employed in the formulations of the disclosure typically comprises glyphosate. Glyphosate is an organic compound that at neutral pH comprises three acidic protonable groups, and in its acid form is relatively insoluble in water. Therefore, glyphosate is normally formulated and applied as a water-soluble salt. Although monobasic, dibasic, and tribasic salts of glyphosate can be made, it has generally been preferred to formulate and apply glyphosate in the form of a monobasic salt, for example as a mono-(organic ammonium) salt such as the mono (isopropylamine), often referred to as IPA, salt, or as either monobasic or dibasic ammonium (NH4) salt. Other suitable glyphosate salts include sodium (Na), potassium (K), monoethanolamine (MEA), diethanolamine (DEA), triethanolamine (TEA), trimesium (TMS), and mixtures thereof. In various embodiments, the glyphosate salt is chosen from sodium, potassium, ammonium, isopropylamine, monethanolamine, diethanolamine, triethanolamine, trimesium salts, and mixtures thereof. In various other embodiments, the glyphosate salt is chosen from ammonium glyphosate, diammonium glyphosate, sodium glyphosate, potassium glyphosate, isopropylammonium glyphosate, and the monethanolamine salt of glyphosate.

I. COTE-Based Adjuvants

The surfactants of the present disclosure comprise at least one COTE-based adjuvant as described herein, and have demonstrated the ability to enhance the bioefficacy of glyphosate formulations while at the same time providing the potential for both conventional and ultrahigh loadings of glyphosate and salts thereof yet having very low irritation to eyes and low toxicity to aquatic life.

In one embodiment, in the Structure I, R1 and R3 independently represent alkanol having about 1-150 carbon atoms and about 1-150 hydroxyl groups; or ether-alkanol having about 1-150 carbon atoms, about 1-150 hydroxyl groups, and about 1-40 ether linkages; and R2 and R4, independently, represent hydrogen; alkyl having about 1-150 carbon atoms; alkanol having about 1-150 carbon atoms and about 1-150 hydroxyl groups; or ether-alkanol having about 1-150 carbon atoms, about 1-150 hydroxyl groups, and about 1-40 ether linkages.

In one embodiment, in the Structure I, R1 and R3 independently represent a member chosen from —(CH$_2$)$_n$OH; —C[(CH$_2$)$_n$OH]$_3$; —(CH—OH)$_n$—CH$_2$—OH;

maltodextrinamine/oligosaccharide amines; and closed chain analogs thereof; and $R^2$ and $R^4$ independently represent a member chosen from hydrogen; alkyl having 1-12 carbon atoms; $-(CH_2)_nOH$; $-C[(CH_2)_nOH]_3$; $-(CH-OH)_n-CH_2-OH$;

maltodextrineamine/oligosaccharide amines; and closed chain analogs thereof; wherein in each case n, independently, represents an integer from about 1-7.

In one embodiment, in the Structure I, $R^1$ and $R^2$ together with the nitrogen atom to which they are attached and/or $R^3$ and $R^4$ together with the nitrogen to which they are attached is an amino alcohol. Examples of amino alcohols include aminoglycerols such as 1-aminoglycerol (also known as 1-amino-2,3-propanediol); 2-aminoglycerol (also known as 2-amino, 1,3-propanediol) and diisopropanolamine. Preferred examples of amino alcohols include the following structures:

wherein n=1-19 or 1-17.

In one embodiment, in the Structure I, R1 and R2 together are identical to R3 and R4 together, resulting in identical termini, although where a composition comprises a plurality of surfactants of Structure I the formulation viewed as a whole may contain different termini.

In one embodiment, in the Structure I, R1 and R2 together are different from R3 and R4 together, resulting in mixed termini.

In one embodiment, the disclosure relates to a surfactant composition comprising at least one surfactant of Structure I.

In another embodiment, the disclosure relates to a surfactant composition comprising a plurality of surfactants of Structure I.

In another embodiment, the surfactant composition comprises in addition to at least surfactant of Structure I also at least one co-surfactant not having Structure I.

II. Methods of Preparation

The surfactants of the disclosure can generally be prepared according to the following Scheme:

Castor Oil Triglycidyl Ether ("COTE")

Glycerol      COTE-Based Surfactant

Castor oil triglycidyl ether has two reaction sites for an amine to react—the ester and the epoxide. Either a single primary or secondary amine or a mixture of primary and/or secondary amines as shown in the scheme can be used to make the inventive surfactant products. Exemplary preparations are provided herein below. Details as to amounts and reaction conditions are within the skill of the average artisan. The reaction can be carried out in the presence or absence of solvents. Suitable solvents include polar protic solvents, such as methanol, ethanol, isopropanol, and glycols, such as ethylene glycol, monopropylene glycol, water and the like, as well as polar aprotic solvents, such as dimethylformamide, tetrahydrofuran, ethyl acetate, amidopropylamine, acetonitrile, and the like. The progress of the reaction can be monitored, for example, with IR by monitoring the disappearance of the COTE ester carbonyl peak, which usually occurs around 1740, and the emergence of the amide carbonyl peak at about 1620.

While not wishing to be bound by theory, we believe that the epoxide function is more reactive than the ester function. Accordingly, the situation has resulted as described hereinbelow for Example 15 wherein the primary or secondary amine primarily reacts at the epoxide, but not the ester yielding compounds of the Structure II:

Structure II wherein each $R^3$ independently represents alkanol or ether-alkanol; and each $R^4$ independently represents hydrogen, alkyl, alkanol or ether-alkanol.

Generally, the preferences for Structure II are the same as given above for R3 and R4 in connection with Structure I.

These compounds of Structure II function in the same manner as the compounds of Structure I and, therefore, the present disclosure relates in another embodiment to a surfactant composition comprising at least one surfactant of Structure II.

The present disclosure relates in another embodiment to a herbicidal composition comprising a herbicidally effective amount of glyphosate or a salt thereof and at least one surfactant of Structure II.

The present disclosure relates in yet another embodiment to a method of preparing a surfactant of Structure II, said method comprising (a) reacting castor oil triglycidyl ether ("COTE") with at least one primary and/or secondary amine and (b) obtaining at least one surfactant compound having the Structure II.

Compounds and compositions that comprise a mixture of at least one compound of Structure I and at least one compound of Structure II are likewise contemplated, as are compounds and compositions that comprise only one or more compounds of Structure I or one or more compounds of Structure II.

It should also be clear that where a mixture of primary and/or secondary amines is utilized, each resulting Structure I molecule will exhibit "handedness," i.e., a first primary and/or secondary amine could replace the ester group and a second primary and/or secondary amine could replace the epoxide function. The disclosure is to be construed to include both (1) the first primary and/or secondary amine replacing the ester group and the second primary and/or secondary amine replacing the epoxide function, as well as (2) the first primary and/or secondary amine replacing the epoxide function and the second primary and/or secondary amine replacing the ester group. The disclosure is also to be construed to include each of these two possibilities in the substantial absence of the other. For example, consider castor oil triglycidyl ether (COTE) reacted with N-methylglucamine (NMG) and diethanolamine (DEA). The reaction could produce DEA-COTE-NMG, NMG-COTE-DEA or a mixture of the two reaction products, the abbreviations here, of course, symbolizing residues of the starting materials post-reaction. The disclosure is intended to cover (1) DEA-COTE-NMG alone; (2) NMG-COTE-DEA alone; or (3) mixtures of DEA-COTE-NMG+NMG-COTE-DEA.

Figure 2:
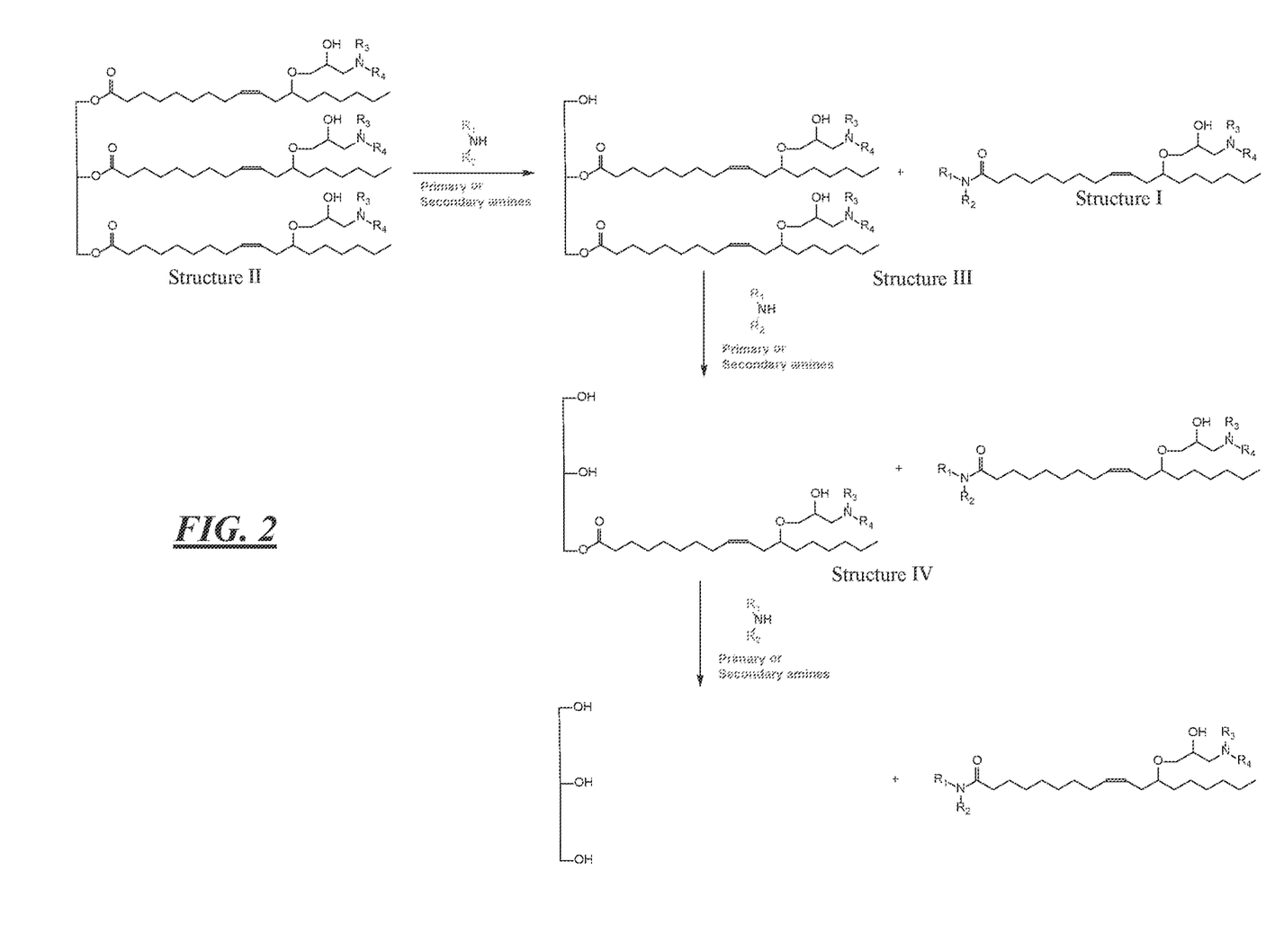
FIG. 2 is a reaction scheme focusing on the compounds of Structure II being converted to compounds of Structure I.

The compounds of Structure II can be converted to compounds of Structure I according to the following reaction scheme set forth in FIG. 2.

Compounds of Structure III and IV form a part of the present disclosure and residual levels of these mono- and diglycerides may be present in the final product.

III. Herbicidal Formulations

The herbicidal formulations of the present disclosure can, in addition to the surfactants set forth in the above formula, contain additional components including, but not limited to, additional surfactants or other additives. It is preferred that when the formulations of the disclosure do contain such additional components, that such additional components are likewise substantially non-irritating to the eye, substantially non-toxic to aquatic life, and have acceptable bioefficacy. Herbicidal formulations of the present disclosures may be in the form of liquid concentrates, solid concentrates, or a "ready-to-use" (i.e., RTU) composition prepared by diluting an aqueous concentrate or dissolving a solid composition.

In one embodiment, the herbicidal composition comprises glyphosate or a salt thereof and at least one surfactant of Structure I and/or Structure II.

In one embodiment, the at least one surfactant of Structure I and/or Structure II is(are) the only surfactant(s) in the herbicidal composition.

In another embodiment, in addition to said at least one surfactant of Structure I and/or Structure II, the herbicidal composition additionally comprises at least one co-surfactant not having either Structure I or Structure II.

Co-Surfactants

Where co-surfactants are present in the herbicidal composition, these can be cationic, anionic, nonionic, and amphoteric surfactants.

Non-limiting examples of preferred cationic surfactants are alkoxylated alkylamine and its quaternary derivative, alkoxylated etheramine and its quaternary derivative, alkoxylated alkyl amines and oxides, alkoxylated alkyl etheramines and oxides, alkyl amidopropyl amines and oxide, alkyl trimethyl ammonium chloride, and alkyl (typically C6 to C10) dimethylaminopropylamine.

Non-limiting examples of preferred anionic surfactants are alkylsulfate, alkylethersulfate, alkylsulfonate, alkylsulfosuccinate, alkoxylated phosphate ester, alkyl alpha olefin sulfonate, alkyl n-methyl taurate, fatty acid isethionate, and alkyl ether carboxylate.

Non-limiting examples of preferred nonionic surfactants are alkoxylated mono and/or diglycerides, sorbitan ester and its alkoxylated derivative, sorbitol ester and its alkoxylated derivative, fatty acid ester, castor oil alkoxylate, alcohol alkoxylate, alkanolamide, alkanolamide alkoxylate, and alkyl polyglycoside.

Non-limiting examples of preferred amphoteric surfactants are alkyl betaine, alkyl amidopropyl betaine, alkylamphoacetate, alkylamphodiacetate, alkylamphocarboxylate, alkylamphopropionate, alkylamphodipropionate, alkyl amidoamine carboxylate, alkylamphohydroxypropyl sulfonate, alkyl sultaine, alkyl amidopropyl hydroxyl sultaine, alkyl dihydroxyethyl glycinate, and alkyl aminopropionate.

In various embodiments, the weight ratio of surfactant of Structure I (and/or Structure II) to total surfactant concentration of the formulation is generally from about 1:9 to about 9:1, typically from about 1:6 to about 6:1 and, typically from about 1:4 to about 4:1 and, more typically, from about 1:2 to about 2:1.

One particularly preferred co-surfactant is amidoalkylamine surfactants, as described further below. The amidoalkylamine surfactants have the general Structure (V):

Structure (V)

wherein $R_1$ is a hydrocarbyl or substituted hydrocarbyl having from 1 to about 22 carbon atoms, $R_2$ and $R_3$ are each independently hydrocarbyl or substituted hydrocarbyl having from 1 to about 6 carbon atoms and $R_4$ is hydrocarbylene or substituted hydrocarbylene having from 1 to about 6 carbon atoms.

R1 is typically an alkyl or substituted alkyl having an average value of carbon atoms between about 4 to about 20 carbon atoms, typically an average value between about 4 and about 18 carbon atoms, more typically an average value from about 4 to about 12 carbon atoms, more typically an average value from about 5 to about 12 carbon atoms, even more typically an average value from about 6 to about 12 carbon atoms, and still more typically an average value from about 6 to about 10 carbon atoms. The R1 alkyl group may be derived from a variety of sources that provide alkyl groups having from about 4 to about 18 carbon atoms, for example, the source may be butyric acid, valeric acid, caprylic acid, capric acid, coco (comprising mainly lauric acid), myristic acid (from, e.g., palm oil), soy (comprising mainly linoleic acid, oleic acid, and palmitic acid), or tallow (comprising mainly palmitic acid, oleic acid, and stearic acid). In some embodiments, the amidoalkylamine surfactant component may comprise a blend of amidoalkylamines having alkyl chains of various lengths from about 5 carbon atoms to about 12 carbon atoms. For example, depending upon the source of the R1 alkyl group, an amidoalkylamine surfactant component may comprise a blend of surfactants having R1 groups that are 5 carbon atoms in length, 6 carbon atoms in length, 7 carbon atoms in length, 8 carbon atoms in length, 9 carbon atoms in length, 10 carbon atoms in length, 11 carbon atoms in length, and 12 carbon atoms in length, longer carbon chains, and combinations thereof. In other embodiments, the amidoalkylamine surfactant component may comprise a blend of surfactants having R1 groups that are 5 carbon atoms in length, 6 carbon atoms in length, 7 carbon atoms in length, and 8 carbon atoms in length. In some alternative embodiments, the amidoalkylamine surfactant component may comprise a blend of surfactants having R1 groups that are 6 carbon atoms in length, 7 carbon atoms in length, 8 carbon atoms in length, 9 carbon atoms in length, and 10 carbon atoms in length. In other embodiments, the amidoalkylamine surfactant component may comprise a blend of surfactants having R1 groups that are 8 carbon atoms in length, 9 carbon atoms in length, 10 carbon atoms in length, 11 carbon atoms in length, and 12 carbon atoms in length.

R2 and R3 are independently typically an alkyl or substituted alkyl having from 1 to about 4 carbon atoms. R2 and R3 are most typically independently an alkyl having from 1 to about 4 carbon atoms, and most typically methyl. R4 is typically an alkylene or substituted alkylene having from 1 to about 4 carbon atoms. R4 is most typically an alkylene having from 1 to about 4 carbon atoms, and most typically n-propylene.

In one preferred amidoalkylamine surfactant, R1 is C6-10, i.e., an alkyl group having 6 carbon atoms, 7 carbon atoms, 8 carbon atoms, 9 carbon atoms, 10 carbon atoms, or a blend of any of these, i.e., from about 6 carbon atoms to about 10 carbon atoms; R2 and R3 are each methyl; and R4 is n-propylene (i.e., C6-10 amidopropyl dimethylamine).

When R4 is n-propylene, the amidoalkylamine surfactants are termed amidopropylamine (APA) surfactants.

Glyphosate Formulations

Generally, the glyphosate loading of herbicidal compositions of the present disclosure is at least about 180 g a.e./L, at least about 220 g a.e./L, at least about 260 g a.e./L, at least about 300 g a.e./L, at least about 320 g a.e./L, at least about 360 g a.e./L, at least about 400 g a.e./L, at least about 480 g a.e./L, at least about 500 g a.e./L, at least about 540 g a.e./L, or at least about 600 g a.e./L. As indicated above, ultrahigh loadings of glyphosate or a glyphosate salt are made possible using the surfactants of Structure I (and/or Structure II), i.e., loadings of glyphosate or a glyphosate salt of at least 540 g a.e./L, although less than ultrahigh loading remains possible if desired.

For example, a typical stable liquid glyphosate formulation according to the disclosure has a concentration of glyphosate in the range of from about 360 to about 600 g a.e./L, typically from about 450 to about 580 g a.e./L. Generally, these formulations contain glyphosate (a.e.) at a concentration of from about 1 to about 65 wt. % or from about 1 to about 60 wt. %. Typically, these formulations contain glyphosate (a.e.) at a concentration of from about 15 to about 50 wt. % or from about 25 to about 50 wt. %.

Generally, stable liquid glyphosate formulations include one or more surfactants of Structure I (and/or Structure II) of the present disclosure at a concentration of from about 1 to about 25 wt. %, typically from about 1 to about 20 wt. % and, more typically, from 5 to about 15 wt. %.

Generally, the weight ratio of glyphosate (a.e.) to surfactant of Structure I (and/or Structure II) of the present disclosure is from about 1:1 to about 100:1, or from about 1:1 to about 50:1. In various embodiments, the weight ratio of these components is from about 1:1 to about 30:1 or from about 1:1 to about 20:1. Typically, the weight ratio of glyphosate (a.e.) to the total proportion of surfactants of Structure I (and/or Structure II) surfactant of the disclosure is between about 1:1 and about 30:1 or between about 2:1 and about 25:1 (e.g., typically between about 2.5:1 and about 20:1, between about 1:1 and about 15:1, between about 2:1 and about 10:1, between about 3:1 and about 15:1, or between about 3.5:1 and about 8:1). In various preferred embodiments, the weight ratio of these components is from about 1:1 to about 15:1, more typically from about 1:1 to about 10:1 and, still more typically, from about 1:1 to about 8:1 (e.g., from about 1:1 to about 6:1, or from about 1:1 to about 4:1). In various other preferred embodiments, the weight ratio of glyphosate (a.e.) to total proportion of surfactants of Structure I (and/or Structure II) is from about 3:1 to about 5:1, or from about 3:1 to about 4:1. In various preferred embodiments, the concentration of glyphosate is in the range of from about 360 to about 600 g a.e./L, and the weight ratio of glyphosate (wt. % a.e.) to the surfactant of Structure I (and/or Structure II) of the present disclosure is between about 2:1 and about 25:1 (e.g., between about 2.5:1 and about 20:1, or between about 3.5:1 and about 8:1).

Along with the glyphosate salt and the surfactant of Structure I (and/or Structure II) compositions of the present disclosure can include another surfactant such as those detailed elsewhere herein.

Formulations of the present disclosure including one or more surfactants of Structure I (and/or Structure II) of the present disclosure along with one or more other optional surfactants also typically include various other conventional components such as, for example, anti-foaming agents and dyes. These components generally individually or in combination comprise from about 0.1 to about 5 wt. % or from about 0.1 to about 2 wt. % of the formulation. The balance of these formulations is water.

Various other embodiments of the present disclosure are directed to solid (i.e., dry) herbicidal formulations comprising glyphosate or a salt thereof, optionally along with one or more other active ingredients. These other active ingredients include those generally known in the art including, for example, coherbicides, fungicides, and plant health agents such as those listed elsewhere herein. An herbicidal composition according to the disclosure can optionally comprise other additives such as ammonium sulfate, potassium sulfate, potassium chloride, sodium sulfate, urea, glycerol, glycols, polyglycols, or mixtures thereof. Generally, any second active agent comprises from about 5 to about 90 wt. % or from about 5 to about 50 wt. % of the composition. Typically, the second active agent comprises from about 5 to about 35 wt. % and, still more typically, from about 10 to about 30 wt. % of the composition. Further in accordance with those embodiments including glyphosate and a second active agent, the weight ratio of glyphosate to second active agent generally is from about 1:1 to about 10:1, from about 1:1 to about 6:1, or from about 2:1 to about 6:1.

The present disclosure encompasses not merely formulations of glyphosate, but also relates to other herbicidal compositions comprising at least one co-herbicidal active, and at least one surfactant, wherein said at least one surfactant comprises the surfactants of the disclosure. The present disclosure also encompasses herbicidal formulations comprising herbicidal actives other than glyphosate including, for example, 2,4-dichlorophenoxyacetic acid (2,4-D), dicamba, and glufosinate.

In one embodiment, the herbicidal composition does not contain any additional co-herbicide besides the glyphosate or salt thereof.

In another embodiment, the herbicidal composition comprises at least one co-herbicide besides the glyphosate or salt thereof.

Regardless of the particular co-herbicide or combination of co-herbicides present in the formulation, the weight ratio of glyphosate (a.e.) to one or more co-herbicides is typically from about 9:1 to 1:9, more typically about 5:1 to 1:5, or about 2:1 to 1:2.

Formulations of the present disclosure may generally be prepared by mixing the glyphosate salt solution, prepared as outlined above, together with other ingredients in a suitable mixing vessel with agitation, such as a blender. Various embodiments of the present disclosure are directed to aqueous concentrate compositions including glyphosate along with one or more surfactants of Structure I and/or Structure II. An herbicidal concentrate of the present disclosure may be prepared by combining the required amounts of glyphosate, water, surfactant, etc., with mixing using a mechanical stirrer or any other suitable container or device producing the necessary amount of agitation or circulation to thoroughly mix the ingredients. The order of addition of the starting materials is not narrowly critical to the stability of the final concentrate A solid concentrate of the present disclosure may also be prepared by combining the required amounts of glyphosate, surfactant, etc. using a mechanical stirrer, ball milling, or any other suitable container or device producing the necessary amount of agitation or circulation to thoroughly mix the ingredients. The order of addition of the materials to prepare the solid concentrate is not narrowly critical to the stability of the final concentrate.

Compositions of the present disclosure ready for use (i.e., RTU compositions) can be prepared by diluting an aqueous herbicidal concentrate or dissolving a solid concentrate with an appropriate amount of water.

The present disclosure is also directed to a method for killing or controlling weeds or other unwanted plants by spraying or otherwise applying a herbicidally effective amount of the RTU or diluted concentrate formulations described herein to the foliage of the plants to be treated. The herbicidal spray compositions included in the present disclosure can be applied to the foliage of the plants to be treated through any of the appropriate methods that are well known to those having skill in the art. In some embodiments, the RTU composition is packaged in a portable container suitable for hand carry by the user and fitted with an apparatus for manually releasing the composition from the container onto the foliage of the plants to be treated in the form of a spray.

The compositions of the present disclosure can be used to kill or control the growth of a wide variety of plants.

Generally, various embodiments of the present disclosure are directed to methods for controlling unwanted vegetation comprising applying an effective amount of the herbicidal formulation to the unwanted vegetation. The glyphosate formulation of the disclosure should be applied to plant foliage at an application rate sufficient to give the desired effect. Application rates are usually expressed as amount of glyphosate ae per unit area of land treated, e.g. grams ae per hectare (g a.e./ha). Suitable herbicidally efficacious application or spray rates used in the practice of the present disclosure will vary depending on the particular composition and concentration of active ingredients, the desired effects, plant species treated, weather and other factors. What constitutes a "desired effect" varies according to the standards and practice of those who investigate, develop, market, and use glyphosate products. For example, the amount of glyphosate a.e. applied per unit area to give, consistently and reliably, at least about 70%, more typically at least about 85% control of a plant species as measured by growth reduction or mortality is often used to define a commercially effective rate.

Preferred compositions of the disclosure provide equivalent herbicidal efficacy by comparison with commercial standard formulations of glyphosate. "Herbicidal efficacy," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants.

The selection of application rates that are biologically effective for a specific glyphosate formulation, such as a formulation of the present disclosure, is within the skill of the ordinary agricultural scientist. Those skilled in the art will likewise recognize that individual plant conditions, weather, and growing conditions, as well as the specific formulation selected, will influence the degree of biological effectiveness achieved in practicing this disclosure. Useful application rates can therefore depend upon all of the above conditions. Much information is known about appropriate application rates for glyphosate formulations in general. Over two decades of glyphosate use and published studies relating to such use have provided abundant information from which a weed control practitioner can select glyphosate application rates that are herbicidally effective on particular species at particular growth stages in particular environmental conditions.

Various application methods may be employed including broadcast spraying, directed spraying or wiping the foliage with a diluted composition of this disclosure. Depending on the degree of control desired, the age and species of the plants, weather conditions and other factors, typically the glyphosate application rate is an herbicidally effective amount of about 0.1 to about 10 kg a.e./ha and typically from about 0.25 to about 2.5 kg a.e./ha, although greater or lesser amounts may be applied.

As noted, the formulation may comprise a glyphosate salt such as ammonium glyphosate, diammonium glyphosate, sodium glyphosate, potassium glyphosate, isopropylammonium glyphosate, and combinations thereof. Other suitable glyphosate salts include the monoethanolamine (MEA), diethanolamine (DEA), triethanolamine (TEA), trimesium (TMS) salts, and combinations thereof.

Definitions

The term "castor oil triglycidyl ether" or the abbreviation "COTE" as used herein mean (a) castor oil triglycidyl ether; (b) hydrogenated castor oil triglycidyl ether; (c) ricinoleic acid/ester monoglycidyl ether; and/or hydroxy stearic acid/ester monoglycidyl ether.

The term "hydrocarbyl" as used herein describes organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties typically comprise 1 to about 30 carbon atoms.

The term "hydrocarbylene" as used herein describes radicals joined at two ends thereof to other radicals in an organic compound, and which consist exclusively of the elements carbon and hydrogen. These moieties include alkylene, alkenylene, alkynylene, and arylene moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties typically comprise 1 to 30 carbon atoms.

The term "substituted hydrocarbyl" as used herein describes hydrocarbyl moieties that are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

The "substituted hydrocarbylene" moieties described herein are hydrocarbylene moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

Unless otherwise indicated, the alkyl groups described herein are typically lower alkyl comprising from one to about 18 carbon atoms in the principal chain and up to about 30 carbon atoms. They may be straight or branched chain or cyclic and include methyl, ethyl, propyl, isopropyl, n-butyl, isobutyl, hexyl, 2-ethylhexyl, and the like.

Unless otherwise indicated, the alkenyl groups described herein are typically lower alkenyl comprising from two to about 18 carbon atoms in the principal chain and up to about 30 carbon atoms. They may be straight or branched chain or cyclic and include ethenyl, propenyl, isopropenyl, butenyl, isobutenyl, hexenyl, and the like. Unless otherwise indicated, the alkynyl groups described herein are typically lower alkynyl comprising from two to about 18 carbon atoms in the principal chain and up to about 30 carbon atoms. They may be straight or branched chain and include ethynyl, propynyl, butynyl, isobutynyl, hexynyl, and the like. The term "aryl" as used herein alone or as part of another group denote optionally substituted homocyclic aromatic groups, typically monocyclic or bicyclic groups comprising from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "aralkyl" as used herein denotes a group comprising both alkyl and aryl structures such as benzyl.

As used herein, the alkyl, alkenyl, alkynyl, aryl and aralkyl groups can be substituted with at least one atom other than carbon, including moieties in which a carbon chain atom is substituted with a hetero atom such as nitrogen, oxygen, silicon, phosphorous, boron, sulfur, or a halogen atom. These substituents include hydroxy, nitro, amino, amido, nitro, cyano, sulfoxide, thiol, thioester, thioether, ester and ether, or any other substituent which can increase the compatibility of the surfactant and/or its efficacy enhancement in the potassium glyphosate formulation without adversely affecting the storage stability of the formulation.

The terms "halogen" or "halo" as used herein alone or as part of another group refer to chlorine, bromine, fluorine, and iodine. Fluorine substituents are often preferred in surfactant compounds.

The term "cyclic" as used herein alone or as part of another group denotes a group having at least one closed ring, and includes alicyclic, aromatic (arene) and heterocyclic groups.

The term "acyl," as used herein alone or as part of another group, denotes the moiety formed by removal of the hydroxyl group from the group —COOH of an organic carboxylic acid, e.g., RC(O)—, wherein R is R1, R1O—, R1R2N—, or R1S—, R1 is hydrocarbyl, heterosubstituted hydrocarbyl, or heterocyclo and R2 is hydrogen, hydrocarbyl or substituted hydrocarbyl.

The term "alkanol" as used herein alone or as part of another group denotes a straight or branched alkyl chain substituted by one or more hydroxyl groups.

The term "ether-alkanol" as used herein alone or as part of another group denotes an alkanol group as defined above interrupted in the straight or branched alkyl chain by an oxygen atom resulting in an "ether (C—O—C) linkage" or joined at one of its carbon atoms via an oxygen atom to a carbon atom of another portion of the molecule. For example, in maltose both (1) the ring oxygen atoms and (2) the oxygen atoms connecting the two glucose units would be considered to be ether linkages; and the maltose residue thus an ether alkanol. The term "ether-alkanol" is broad enough to embrace acetals, hemiacetals, or hemiketals.

The present disclosure will now be illustrated by the following non-limiting examples.

The disclosure will now be described in greater detail with reference to the following non-limiting examples.

EXAMPLES

Abbreviations

COTE Castor oil triglycidyl ether
NMG N-methylglucamine
DEA Diethanolamine
TRIS Tris(hydroxymethyl)aminomethane
NML N-methyllactamine
MPG Monopropylene glycol
APA-7 Amidopropylamine (AkzoNobel)
APA-9 Amidopropylamine (AkzoNobel)
LSD Least Significant Difference Compound Examples A. General Procedures Castor oil triglycidyl ether (COTE) and primary or secondary alkanol amine or a mixture thereof are combined optionally in a suitable solvent, for example, methanol, ethanol, isopropanol, ethylene glycol, monopropylene glycol, or amidopropylamine, or a mixture thereof, in a round bottom flask immersed in an oil bath operating between 100-150° C. with stirring, optionally magnetic or overhead, under a nitrogen atmosphere until a clear liquid or semi-solid is obtained. Progress of the reaction is monitored by IR, looking for a reduction in the ester carbonyl peak around 1740 and the appearance of the amide carbonyl peak around 1620. When the reaction is completed, the product is worked-up and collected. The products thus obtained can optionally be further diluted by adding necessary amount of water. When more than one amine is used, the amines can be added sequentially or all at once.

B. COTE-Based Adjuvants

Following the general procedures outlined above, the following COTE-based adjuvants corresponding to Structure I were produced.

| Example | COTE (g) | NMG (g) | NML (g) | DEA (g) | TRIS (g) | MPG (g) | APA-7 (g) | APA-9 (g) | Water (g) |
|---|---|---|---|---|---|---|---|---|---|
| 1 | 55.50 | 29.25 | | 20.38 | | | | | |
| 2 | 55.50 | | | 29.10 | | | | | |
| 3 | 55.50 | 58.50 | | | | | | | |
| 4 | 55.50 | 58.55 | | | | | | 22.81 | |
| 5 | 55.50 | 29.25 | | | 18.15 | | | 11.43 | |
| 6 | 11.00 | | 10.71 | 3.15 | | | | 6.21 | |
| 7 | 77.00 | 40.95 | | | 25.41 | 39.20 | | | |
| 8 | 77.00 | 40.95 | | 25.72 | | 14.37 | | | 14.37 |
| 9 | 77.00 | 27.30 | | 33.07 | | 13.74 | | | 13.74 |
| 10 | 88.00 | | | 29.40 | 29.00 | 14.64 | | | 14.64 |
| 11 | 66.00 | 70.20 | | | | 13.62 | | | 13.62 |
| 12 | 66.00 | 70.20 | | | | | | 34.05 | 24.32 |
| 13 | 77.00 | 40.95 | | 22.05 | | | | 35.00 | 11.67 |
| 14 | 77.00 | 27.30 | | 29.40 | | | | 35.65 | 8.92 |

In addition, the following COTE-based adjuvants corresponding to Structure II were also produced.

| Example | COTE (g) | NMG (g) | NML (g) | DEA (g) | TRIS (g) | MPG (g) | APA-7 (g) | APA-9 (g) | Water (g) |
|---|---|---|---|---|---|---|---|---|---|
| 15 | 55.50 | 34.14 | | | | | | | |

Example 16: Cloud Point Measurement

Glyphosate formulations were prepared comprising glyphosate salt (K-glyphosate—46.06 wt % AE), surfactant (either single surfactant or surfactant blends), compatibility agent, and water according to the following order of addition:

1. appropriate amount (wt %) of DI water
2. appropriate amount (wt %) of glyphosate salt solution
3. appropriate amount (wt %) of surfactant
4. appropriate amount (wt %) of amidoalkylamine (compatibility agent)

The components were added to a glass vial (8 DRAM—25×95 mm), and the formulation was thoroughly mixed by shaking it vigorously until clear and homogeneous. If necessary the vial was warmed to facilitate mixing. If the formulation was still not clear it was then allowed to stand for 24 hours and if the formulation was still not clear it was described as "unstable/hazy."

The cloud point of all formulations was determined in the following manner: A temperature probe was inserted through the cap into the vial containing the formulation and was placed in a hot water bath (T=80-85° C.). It was allowed to heat until the temperature of the solution reached that of the bath. If the formulation remained clear, the cloud point was designated as >80° C. If the solution became cloudy, it was removed from the bath and allowed to cool while shaking and monitoring the temperature. A temperature reading was taken when the solution cleared and was a measure of the cloud point.

Testing in the foregoing manner yielded the following results:

| Example # | Surfactant % active | wt % | K-Glyphosate wt % | Water wt % | Compatibility Agent Amido alkylamine | % active | wt % | Appearance at RT | Cloud Point ° C. |
|---|---|---|---|---|---|---|---|---|---|
| 15 | 100 | 10.0 | 84.0 | 6.0 | | | | Hazy | ND |
| 2 | 100 | 10.0 | 84.0 | 6.0 | | | | Hazy | ND |
| 1 | 100 | 10.0 | 90.0 | 0.0 | | | | Clear | 76 |
| 3 | 100 | 10.0 | 90.0 | 0.0 | | | | Clear | ND |
| 7 | 75 | 10.0 | 90.0 | 0.0 | | | | Clear | ND |
| 7 | 75 | 10.0 | 84.0 | 6. | | | | Clear | ND |
| 11 | 76.9 | 14.3 | 84.0 | 1.7 | | | | Clear | >80 |
| 8 | 83.3 | 12.5 | 84.0 | 3.5 | | | | Clear | 73 |
| 9 | 83.3 | 12.5 | 84.0 | 3.5 | | | | Clear | 35 |
| 10 | 83.3 | 12.5 | 84.0 | 3.5 | | | | Hazy | <RT |
| 9 | 83.3 | 11.8 | 84.0 | 3.6 | APA-7 | 100 | 0.6 | Clear | 73 |
| 9 | 83.3 | 11.5 | 84.0 | 3.7 | APA-7 | 100 | 0.8 | Clear | >80 |
| 10 | 83.3 | 9.8 | 84.0 | 4.0 | APA-7 | 100 | 2.2 | Clear | 75 |
| 11 | 76.9 | 14.3 | 85.6 | 0.1 | | | | Clear | >80 |
| 8 | 83.3 | 12.5 | 87.5 | 0.0 | | | | Clear | 35 |
| 8 | 83.3 | 12.0 | 87.5 | 0.1 | APA-7 | 100 | 0.4 | Clear | 60 |
| 8 | 83.3 | 11.3 | 87.5 | 0.2 | APA-7 | 100 | 1.0 | Clear | >80 |
| 9 | 83.3 | 10.4 | 87.5 | 0.4 | APA-7 | 100 | 1.7 | Clear | >80 |
| 10 | 83.3 | 8.6 | 87.5 | 0.8 | APA-7 | 100 | 3.1 | Clear | >80 |

Example 17: Stability Measurement

Stability was determined by placing the vials comprising the formulation inside an oven at elevated temperature (40° C.). Observation was taken at 1 week intervals for 3 weeks. If the formulation remained clear and homogeneous, it was designated as "stable."

Testing in the foregoing manner yielded the following results:

| Example # | Surfactant % active | wt % | K-Glyphosate wt % | Water wt % | Interval 1 wk | 2 wks | 3 wks |
|---|---|---|---|---|---|---|---|
| 1 | 100 | 10.0 | 90.0 | 0.0 | Clear | Clear | Clear |
| 3 | 100 | 10.0 | 90.0 | 0.0 | Clear | Clear | Clear |
| 7 | 75 | 10.0 | 90.0 | 0.0 | Clear | Clear | Hazy |
| 7 | 75 | 10.0 | 84.0 | 6.0 | Clear | Clear | Hazy |

Example 18: Bioefficacy

All bioefficacy testing was done at University of Georgia's Agricultural Experiment Station in Griffin, Georgia Concentrates were first formulated by blending IPA glyphosate salt with the desired amount surfactant and water resulting in a 20 wt % ae and a 6.49% surfactant solution. Prior to spraying two sets of diluted solutions were prepared by dissolving 16 g of concentrates into 984 grams of tap water and a second set by dissolving 500 g of the above dilute solution into 500 g of tap water. The samples were sprayed onto wheat representing narrow leaf weeds (4 plants per sample) at a specific fixed rate which resulted in application rate of 600 and 300 g ae/H. The experiment had two control groups: one set of plants that were left untreated and one set that were treated with an IPA glyphosate/Ethomeen T25 (bench-mark) surfactant blend. All of the plants were placed in a temperature controlled greenhouse and measured for growth (or lack of) each week for a period of 4 weeks. The data is reported as % Growth Control compared to untreated plant. The higher the value the better the bioefficacy. When the last measurement was taken at 4 weeks the plants are cut at the roots and the "fresh" weight measured.

Testing in the foregoing manner yielded the following results:

Plant Species—Wheat
IPA-glyphosate application rate—300 g a.e./H

| IPA Glyphosate + Adjuvant | % Growth Control |
|---|---|
| Example 1 | 91 |
| Ethomeen T/25 | 91 |
| IPA-Glyphosate only | 31 |
| 5% LSD | 4.39 |

Plant Species—Wheat
IPA-glyphosate application rate—600 g a.e./H

| IPA Glyphosate + Adjuvant | % Growth Control |
|---|---|
| Example 1 | 95 |
| Ethomeen T/25 | 98 |
| IPA-Glyphosate only | 72 |
| 5% LSD | 3.33 |

Figure 1:
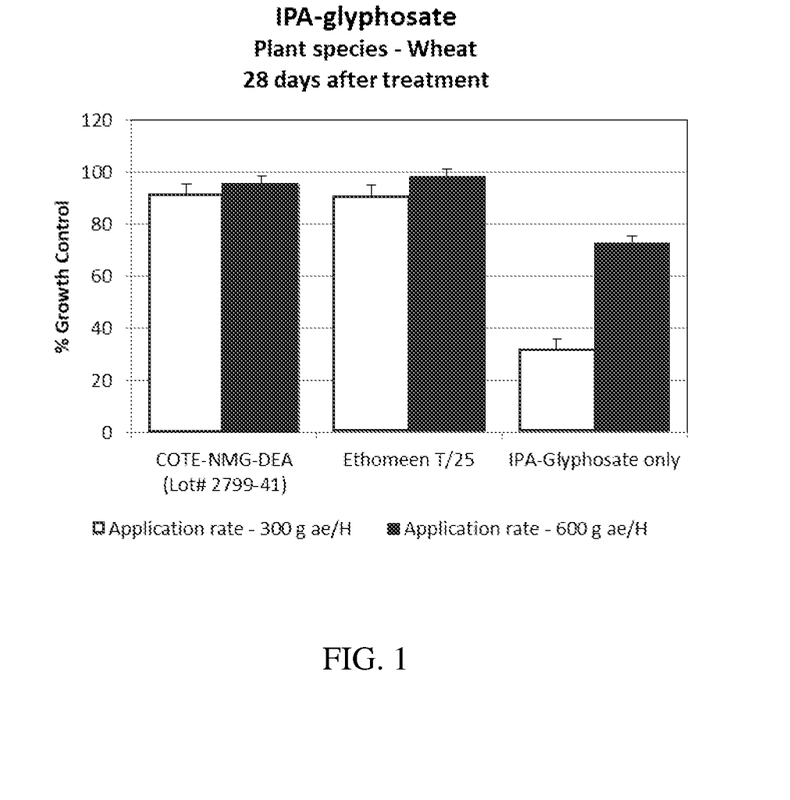
FIG. 1 is a graph depicting the comparative bioefficacy against wheat plants of various glyphosate formulations.

The foregoing data are depicted graphically in FIG. 1.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A surfactant compound having Structure I:

wherein $R^1$ and $R^3$ independently represent alkanol or ether-alkanol; and $R^2$ and $R^4$ independently represent hydrogen, alkyl, alkanol or ether-alkanol.

2. The surfactant compound according to claim 1, wherein $R^1$ and $R^3$ independently represent an alkanol having about 1-150 carbon atoms and about 1-150 hydroxyl groups; or an ether-alkanol having about 1-150 carbon atoms, about 1-150 hydroxyl groups, and about 1-40 ether linkages; and $R^2$ and $R^4$ independently represent hydrogen; an alkyl having about 1-150 carbon atoms; an alkanol having about 1-150 carbon atoms and about 1-150 hydroxyl groups; or an ether-alkanol having about 1-150 carbon atoms, about 1-150 hydroxyl groups, and about 1-40 ether linkages.

3. The surfactant compound of claim 1 having Structure I.

4. The surfactant compound according to claim 3, wherein $R^1$ and $R^3$ independently represent an alkanol having about 1-150 carbon atoms and about 1-150 hydroxyl groups; or an ether-alkanol having about 1-150 carbon atoms, about 1-150 hydroxyl groups, and about 1-40 ether linkages; and $R^2$ and $R^4$ independently represent hydrogen; an alkyl having about 1-150 carbon atoms; an alkanol having about 1-150 carbon atoms and about 1-150 hydroxyl groups; or an ether-alkanol having about 1-150 carbon atoms, about 1-150 hydroxyl groups, and about 1-40 ether linkages.

5. A surfactant compound having Structure II:

wherein $R^3$ represents an alkanol or ether-alkanol; and $R^4$ represents hydrogen, an alkyl, alkanol or ether-alkanol.

6. The surfactant compound according to claim 5, wherein $R^3$ represents an alkanol having about 1-150 carbon atoms and about 1-150 hydroxyl groups; or an ether-alkanol having about 1-150 carbon atoms, about 1-150 hydroxyl groups, and about 1-40 ether linkages; and $R^4$ represents hydrogen; an alkyl having about 1-150 carbon atoms; an alkanol having about 1-150 carbon atoms and about 1-150 hydroxyl groups; or an ether-alkanol having about 1-150 carbon atoms, about 1-150 hydroxyl groups, and about 1-40 ether linkages.

7. A surfactant compound having Structure III:

wherein $R^3$ represents an alkanol or ether-alkanol; and $R^4$ represents hydrogen, an alkyl, alkanol or ether-alkanol.

8. The surfactant compound according to claim 7, wherein $R^3$ represents an alkanol having about 1-150 carbon atoms and about 1-150 hydroxyl groups; or an ether-alkanol having about 1-150 carbon atoms, about 1-150 hydroxyl groups, and about 1-40 ether linkages; and $R^4$ represents hydrogen; an alkyl having about 1-150 carbon atoms; an alkanol having about 1-150 carbon atoms and about 1-150 hydroxyl groups; or an ether-alkanol having about 1-150 carbon atoms, about 1-150 hydroxyl groups, and about 1-40 ether linkages.

9. A surfactant composition comprising at least one surfactant of Structure I, II, or III according to claim 1.

10. The surfactant composition according to claim 9, which additionally comprises at least one co-surfactant not having Structure I, II, or III.

11. A herbicidal composition comprising glyphosate or a salt thereof and at least one surfactant of Structure I, II, or III according to claim 1.

12. The herbicidal composition according to claim 11, wherein said at least one surfactant of Structure I, II or III is/are the only surfactant(s) in the composition.

13. The herbicidal composition according claim 12, which in addition to said at least one surfactant of Structure I, II or III additionally comprises at least one co-surfactant not having Structure I, II or III.

14. The herbicidal composition according to claim 11, which in addition to said glyphosate or salt thereof further comprises at least one additional herbicidally active ingredient.

15. The composition according to claim 14, wherein the at least one additional herbicidally active ingredient is chosen from 2,4-dichlorophenoxyacetic acid (2,4-D), dicamba, glufosinate, and combinations thereof.

16. The composition according to claim 11, wherein the glyphosate salt is chosen from sodium, potassium, ammonium, isopropylamine, monoethanolamine, diethanolamine, triethanolamine, trimesium salts, and mixtures thereof.

17. The composition according to claim 11, which has a loading of glyphosate or a salt thereof of at least about 540 g a.e./L.

18. A method of controlling unwanted vegetation, said method comprising applying to said unwanted vegetation a herbicidally effective amount of a herbicidal composition according to claim 12.

19. A method of preparing a surfactant according to claim 1, said method comprising (a) reacting castor oil triglycidyl ether (COTE) with at least one primary and/or secondary amine and (b) obtaining at least one surfactant compound having the Structure I, II or III.

\* \* \* \* \*